United States Patent [19]

Halloran

[11] Patent Number: 4,484,134
[45] Date of Patent: Nov. 20, 1984

[54] ELONGATE PARTICLE SENSING APERTURE

[75] Inventor: Michael T. Halloran, Pembroke Pines, Fla.

[73] Assignee: Coulter Electrnonics, Inc., Hialeah, Fla.

[21] Appl. No.: 297,651

[22] Filed: Aug. 31, 1981

[51] Int. Cl.³ .............................................. G01N 27/00
[52] U.S. Cl. ..................................... 324/71.1; 377/12
[58] Field of Search .................... 324/71.1, 71.4, 449; 377/10, 11, 12

[56] References Cited

U.S. PATENT DOCUMENTS

| 2,656,508 | 10/1953 | Coulter | 324/71.1 |
| 3,793,587 | 2/1974 | Thom et al. | 324/71.1 |
| 3,958,177 | 5/1976 | Reeves et al. | 324/71.1 |
| 4,140,966 | 2/1979 | Godin et al. | 324/71.1 |
| 4,290,011 | 9/1981 | Berg et al. | 324/71.1 |

FOREIGN PATENT DOCUMENTS

| 66038 | 3/1969 | German Democratic Rep. | 324/71.4 |
| 355959 | 5/1973 | Sweden | 324/71.1 |

OTHER PUBLICATIONS

Menke et al., "A Volume-Activated Cell Sorter", The Journal of Histochemistry and Cytochemistry, 1977, pp. 796–803, vol. 25, No. 7.

Primary Examiner—Michael J. Tokar
Assistant Examiner—Kevin D. O'Shea
Attorney, Agent, or Firm—Gerald R. Hibnick

[57] ABSTRACT

Disclosed is a particle analyzing apparatus having a flow cell with an elongated or tube-like aperture for receiving a liquid suspension of particles and for providing a smooth fluid flow therethrough and electric field and current, generated in and essentially limited to a relatively small portion of the aperture, for producing electrical signals when the particles pass therethrough.

15 Claims, 5 Drawing Figures

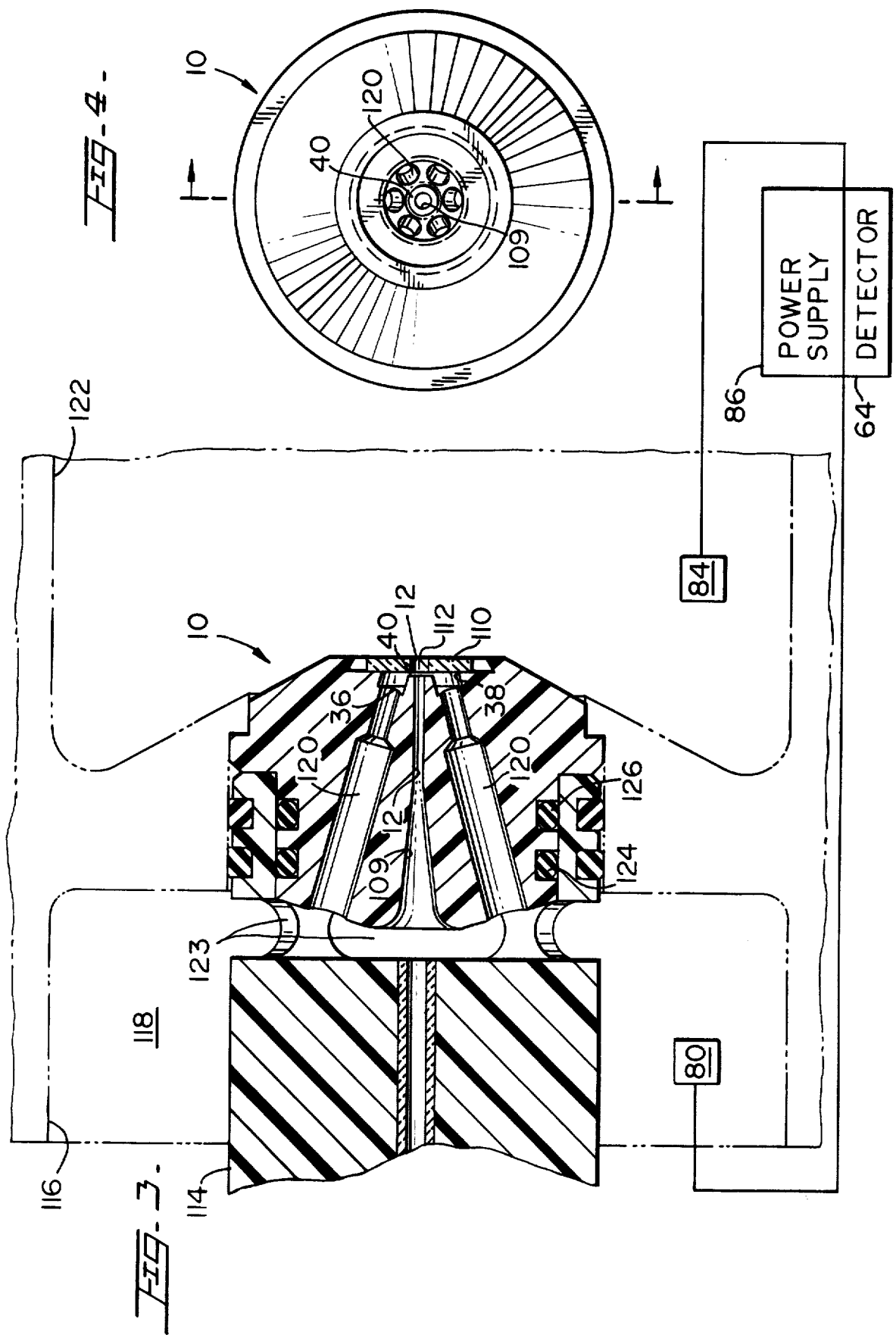

ELONGATE PARTICLE SENSING APERTURE

FIELD OF THE INVENTION

The present invention relates to particle analyzing apparatuses wherein impedance measurements are made on a liquid suspension of particles to obtain electrical pulses representative of the number and characteristics of the particles.

BACKGROUND OF THE INVENTION

Since its conception more than 27 years ago, the principle of particle counting and sizing invented by Wallace H. Coulter has resulted in numerous methods and apparatuses for the electronic counting, sizing and analysis of microscopic particles, which are scanned in a fluid suspension, as shown by the pioneer U.S. Pat. No. 2,656,508 to Coulter. In this prior art arrangement, a D.C. electric current flow is established between two vessels by suspending electrodes in the respective bodies of the suspension fluid. The only fluid connection between the two bodies is through a sensing orifice; hence, an electric current flow and field are established in the orifice. The orifice and the resultant electric field in and around it constitute a sensing zone. As each particle passes through the sensing zone, for the duration of the passage, the impedance of the contents of the sensing zone will change, thereby modulating the current flow and electric field in the sensing zone, and hence causing the generation of a signal to be applied to a detector suitably arranged to respond to such change. (The mark "Coulter" is a registered trademark, Registration No. 995,825, of Coulter Electronics, Inc. of Hialeah, Florida.)

To date, sensing orifices have been made in such a way that their entrances and exits were rather abrupt, so as to minimize the rise time associated with any particular particle's signal. From a fluid dynamics standpoint, orifices with sharp edges, or even rounded edges, are undesirable.

For a classical aperture opening into a semi-infinite space, for flow into the aperture, it is fairly well known that the flow pattern is such that the streamlines are roughly radial and the isobars are roughly hemispherical. In other words, the flow field is not at all similar to the same aperture system with flow from the aperture into the quiescent fluid space.

The important effect of the nearly hemispherical isobars is that the velocity gradient experienced by a particle drawn into the aperture is quite steep. In practice, large and/or dense particles simply do not accelerate as quickly as does the suspending fluid. This is especially true of the high Reynolds numbers ($>>1$) associated with apertures much larger than 100 $\mu$m in diameter. The significance of the substantial Reynolds number is that the inertia forces acting on the fluid and the particle become relatively more important than the fluid shear forces acting on fluid or particle, with increasing Reynolds number.

It has been experimentally verified that large and/or dense particles traverse a sharp edged aperture at velocities substantially lower than the peak fluid velocity, or even the bulk fluid velocity. The slow pulse rise times associated with these slow-moving particles can cause difficulties in the signal processing electronics, and the long pulse lengths can cause problems with coincidence. Attempts to increase the particle velocity in the aperture by increasing the aperture flow rate have met with rapidly diminishing returns, since the pressure drop required increases rapidly, and there is a greater velocity shortfall for higher flow rates.

It should be noted that the highly esteemed "hydrodynamic focusing" technique that works so well at low Reynolds numbers becomes a dismal failure at high Reynolds numbers, because of the steep velocity gradient associated with the "focusing" zone. This ties together some problems associated with an aperture's entrance.

There is also a problem associated with the aperture's exit. The velocity distribution associated with a stream of fluid leaving an aperture and entering a quiescent pool of similar or identical fluid is generally pencil-like. If the receiving chamber is smaller than semi-infinite, the presence of a highly directional jet entering the chamber will induce a generally toroidal circulation within the chamber. In a particle counter of the electrical sensing zone type, it is known that the sensing zone extends beyond both ends of the aperture (symmetrically, unlike the fluid flow fields), has isopotential surfaces which are roughly hemispherical, and can detect the presence of a particle without the aperture and removed by an aperture diameter or more. The toroidal recirculation will eventually carry particles which have already been counted back into the downstream area of the sensing zone, causing them to be counted again and again. A technique called "sweep flow" can prevent this recirculation, but is not likely to be fully effective at high Reynolds numbers, requires complex plumbing and does not diminish the size of the downstream sensing zone.

Accordingly, it can be seen that there is a need in the art for a flow cell which attacks and overcomes all of the problems just discussed and reiterated as follows: (A) velocity shortfall due to steep gradients in the aperture entrance, causing slow-rising pulses and donsequent distortion of small signals by AC-coupled electronics; (B) recirculation of particles behind the aperture, causing multiple false counts; and (C) electrical sensing zone substantially longer than the aperture's physical length, aggravating so-called vertical coincidence and making it difficult to circumvent the effects of same Velocity shortfall also aggravates this problem.

Swedish Pat. No. 355,959 to Everaerts discloses a capacitor formed from two concentric, metal, ring-like electrodes surrounding a moving liquid sample, which are energized with a high frequency source to determine the conductivity of the sample by measuring its capacitance and resistance in a resonating circuit. A typical "focused flow" in which particles are hydrodynamically focused as they pass through a sensing orifice is shown in the article entitled "A Volume-Activated Cell Sorter", THE JOURNAL OF HISTOCHEMISTRY AND CYTOCHEMISTRY, Menke et al, Vol. 25, No. 7, pp. 796–803, 1977.

East German Pat. No. 66,038 a plurality of electrodes mounted along the entire length of an aperture for sensing particles in multiple sensing zones.

U.S. Pat. No. 4,140,966 to Godin et al is incorporated herein.

SUMMARY OF THE INVENTION

The invention is directed toward a flow cell for detecting the properties of a particulate suspension, wherein the particulate suspension passes through an elongated aperture having a tube-like configuration. In a first embodiment, a pair of closely spaced gaps are provided along the axial length of the elongated aperture, with the gaps being in fluid communication with at least one pair of remotely positioned electrodes. The electrodes have a voltage difference applied therebetween so as to generate an electrical field and current primarily between the two gaps; thereby providing a particle sensing zone with a relatively short length dimension compared to the axial length of the elongated aperture. Alternatively, a pair of metal electrodes can be used in place of the liquid-filled gaps.

In a second embodiment according to the invention, a fluid-filled, single gap or metal electrode interrupts the aperture toward its downstream end, so that a particle sensing zone is defined primarily between the single gap or metal electrode and the downstream end of the aperture.

In a third embodiment according to the invention, the aperture is formed by a pair of large diameter bores, a blocking extension interposed between the two bores so as to define a small diameter sensing orifice and a porous insert mounted in each bore with an interiorly-formed channel aligned with the sensing orifice and having a similar cross-sectional configuration and dimensions at the position of joinder, so as to provide a smooth and continuous fluid path.

In each of the embodiments, the elongated aperture or aperture tube is essentially divided into a particle sensing portion and at lease one non-particle sensing portion, with the non-particle sensing portion being upstream of the particle sensing portion and preferably being at least an order of magnitude greater in length. By virtue of this arrangement, the aperture is provided with a sharp edge electrical field, for good pulse response, and a long, smooth fluid path to promote a smooth fluid flow. Optionally, a similar second non-particle sensing zone can be included downstream of the particle sensing portion to inhibit recirculation behind the particle sensing portion. In some embodiments, the use of a liquid-filled gap or gaps for fluid electrodes allows for the metal power electrodes to be remotely disposed from the particle sensing zone, thereby preventing harmful electrolyte products from entering the sensing zone.

The above described embodiments have several advantages ove the prior art flow cells. First, the aperture's "tube-like" configuration allows for higher particle velocities through the sensing zone of the aperture. Second, the flow cell has a real physical limit on the electrical length of the sensing zone. It has been experimentally demonstrated that the electrical sensing zone does not substantially extend upstream of the upstream electrode or downstream of the downstream electrode, if any. This places a physical constraint on the length of the sensing zone, which both reduces the incidence of signal coincidence and makes it easier to correct for mathematically. The pulse rise times with this device are quicker than equivalent prior art for two reasons: (1) the greater particle velocity at the sensing zone's entrance and (2) the length of the sensing zone's "front porch" is essentially equal to the length of the upstream gap and is not threshold-dependent as in an infinite half-space. Depending upon the embodiment, a downstream non-particle sensing portion in the aperture prevents particle recirculation problems.

DESCRIPTION OF THE DRAWINGS

Further objects and advantages of the present invention will become apparent as the following description proceeds, taken in conjunction with the accompanying drawing in which:

FIG. 3 is a cross-sectional view of a second embodiment of the flow cell.

FIG. 4 is an end view of the second embodiment of FIG. 3, shown with the water removed for clarity.

DETAILED DESCRIPTION OF THE PREFERRED EMBODIMENT

Figure 1:
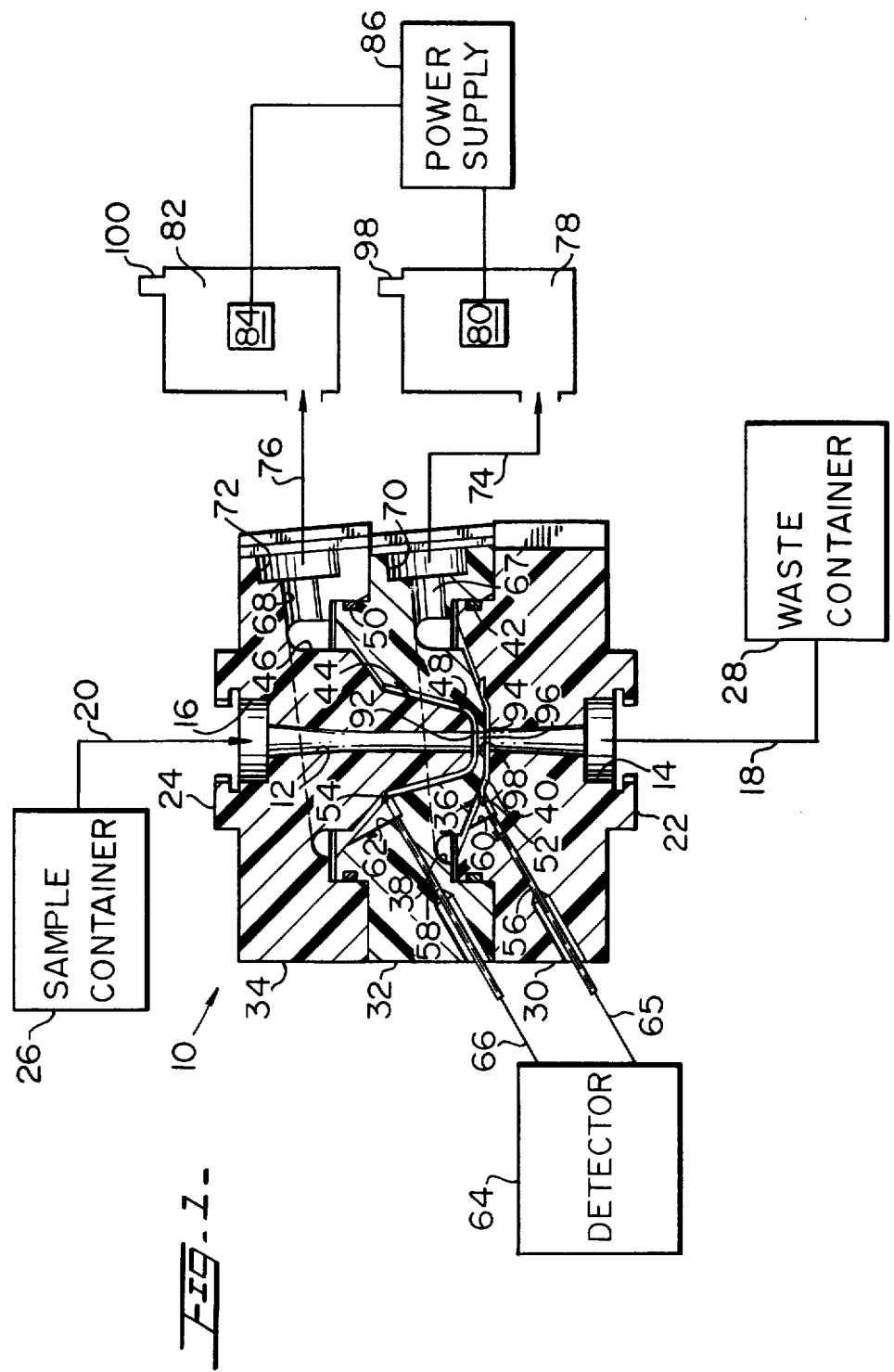
FIG. 1 is a cross-sectional, side view of the first embodiment flow cell according to the invention.

Referring to the FIG. 1, a flow cell 10 is disclosed having a tube or elongated aperture 12 formed therein, which terminates at its opposed ends in a pair of circular cavities 14 and 16. The aperture 12 preferably has a circular cross-sectional configuration, although it can assume other configurations, such as a square configuration. The cavities 14 and 16 are dimensioned and configured for receiving the ends of a pair of fluid conduits 18 and 20, which are schematically shown. A pair of conduit fittings 22 and 24 are used to secure the fluid conduits 18 and 20 to the flow cell 10. Preferably, the elongated aperture 12 has a continuously increasing diameter toward its ends to allow for more hydrodynamically smooth fluid connections between the aperture 12 and the fluid conduits 18 and 20. By use of a conventional hydraulic system, a liquid suspension of particles, such as biological cells or sand, is provided from a sample container 26 and proceeds through the elongated aperture 12, through the fluid conduit 18, and into a waste container 28. The hydraulic system, which creates a pressure drop for moving the sample suspension from the sample container 26 to the waste container 28, can be of any suitable known design, such as illustrated in U.S. Pat. No. 2,656,508 to Coulter et al., and U.S. Pat. No. 4,140,966 to Godin et al.

The flow cell 10 is formed from three plastic blocks 30, 32 and 34. The blocks 30 and 32 mate to define therebetween a first annular chamber 36, having an enlarged, ring-like cavity portion 38 and a relatively thin annular channel portion 40. An O-ring 42 provides a water-tight seal between the blocks 30 and 32. Likewise, the blocks 32 and 34 mate to define therebetween a second annular chamber 44, having an enlarged, ring-like cavity portion 46 and a relatively thin annular channel portion 48. An O-ring 50 provides a water-tight seal between the blocks 32 and 34. The channel portions 40 and 48 open into the elongated aperture 12, so as to form relatively close, consecutive fluid connections along the longitudinal axis of the aperture 12. The blocks are attached to each by a plurality of nuts and bolts (not shown) which traverse all three blocks.

A pair of sensing electrodes 52 and 54, preferably circular in configuration and formed platinum, are mounted in the channel portions 40 and 48, respectively. A pair of drill holes 56 and 58 extend through the blocks 30 and 32, respectively, into cut-outs 60 and 62. A standard detector 64 for measuring changes in electrical impedance is electrically connected to the sensing electrodes 52 and 54 by a pair of electrical wires 65 and 66, respectively, which pass through holes 56 and 58, respectively. A pair of annular channels 67 and 68 open at one end into the cavity portions 38 and 46, respectively, and terminate at the other end in a pair of circular cavities 70 and 72, respectively. The circular cavities 70 and 72 receive the ends of a pair of fluid conduits 74 and 76, respectively. The fluid conduit 74 is in fluid communication with an electrolyte-containing vessel 78, which contains a power electrode 80. The fluid conduit 76 is in fluid communication with an electrolyte-containing vessel 82, which contains a power electrode 84. A power source 86 energizes the electrodes 80 and 84 with a D.C. or low frequency current, such as shown in the previously mentioned U.S. Pat. No. 2,656,508. Alternatively, the electrodes can be energized by a D.C. or low frequency current and/or a high frequency current, such as shown in U.S. Pat. No. 3,502,973 to Coulter et al. and U.S. Pat. No. 3,502,974 to Coulter et al.

The use of two sensing electrodes and two power electrodes and their associated electronics is taught in U.S. Pat. No. 4,019,134 to Hogg. This electrode arrangement is one design which allows for the generation of pulse signals that are substantially independent of the electrolyte conductivity. However, it should be understood that, if desired, just the two power electrodes 80 and 84 can be used, according to the teachings of the previously mentioned U.S. Pat. No. 2,656,508. In either case, it is desirable to have the power electrodes 80 and 84 remotely positioned with respect to the aperture 12, such as accomplished by having the electrodes in the vessels 78 and 82. This isolates the aperture 12 from harmful electrolyte products, such as gas bubbles, created around the power electrodes 80 and 84.

In operation, the vessels 78 and 82; the aperture 12; add the passageways therebetween, including the annular chambers 36 and 44, are filled with an electrolyte solution typically, but not necessarily, having a greater conductivity than the particles being analyzed. An electrical field and current is generated by the power electrodes 80 and 84 substantially in the region of the aperture 12 which is between a pair of parallel, annular openings or gaps 92 and 94 of the channel portions 40 and 48, respectively, into the aperture 12. This region defines a sensing zone 96 wherein the passage of the particle, which is suspended in the moving electrolyte solution, changes the electrical impedance of this region. During the passage of the particle through the sensing zone 96, the particle generates a signal pulse which is detected by the detector 64. As is well known, the detector 64 can include circuitry for measuring the number, size and like parameters of the particle. The gas evolved in the vessels 78 and 82 at the power electrodes by electrolysis can be periodically vented through a pair of normally closed outlets 98 and 100, or through standpipes of suitable elevation.

As previously described, the operative portion of the aperture 12 for sensing the presence of the particles, i.e., sensing zone 96, substantially lies along the axial length of the aperture 12 between the gaps or openings 92 and 94 formed by the annular channels 40 and 48. Operatively, the openings 92 and 94 become the electrodes of the flow cell 10. Although the axial length of the openings is shown to be sizable in FIG. 1 for the purpose of illustration, preferably, but not necessarily, this axial length can be on the order of 5 percent of the diameter at the center of a large aperture, i.e., for example one having a 4000 micron diameter. With elongated apertures having smaller diameters, it is necessary for this axial length to comprise a greater percentage of the aperture's diameter, due to the need for reasonable assembly tolerances. The total axial length of the aperture 12 can vary substantially. For instance, with a 4000 micron diameter aperture, the embodiment of the FIG. 1 was constructed with a 6 centimeter axial length for the aperture 12. However, both smaller and larger embodiments have been built and tested.

It is contemplated that it can be desirable to add a small electrolyte flow through the openings 92 and 94 to reduce fluidic instabilities therein. However, as shown in the illustrative embodiment, such a flow is not necessary.

Figure 2:
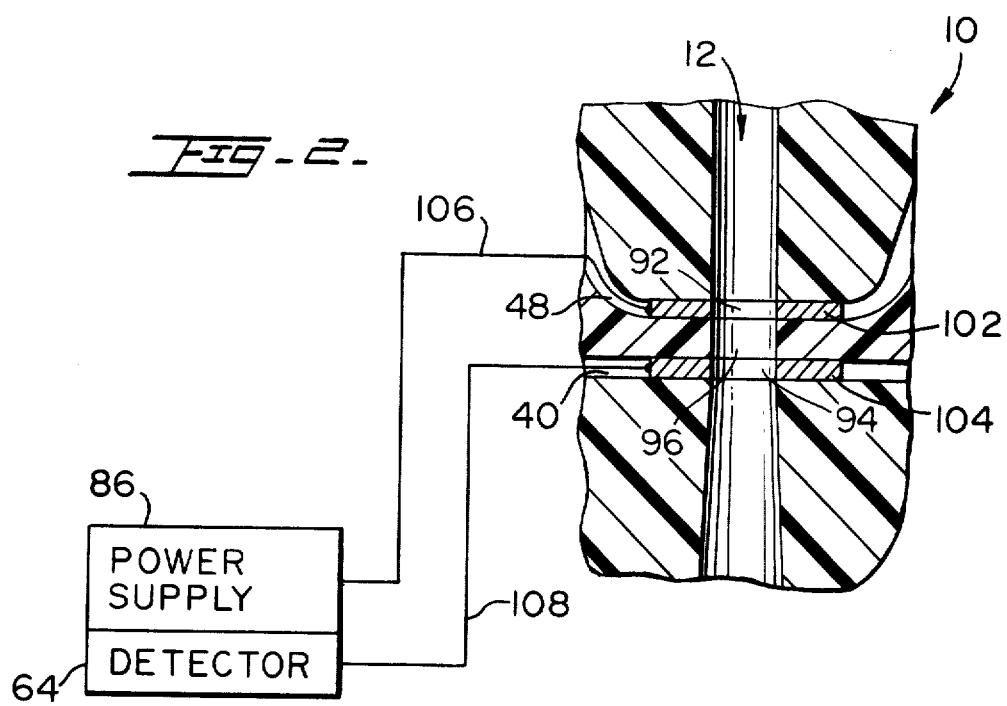
FIG. 2 is a cross-sectional, fragmentary view of a modification to the flow cell of the first embodiment of FIG. 1.

FIG. 2 illustrates an alternative design for the first embodiment of FIG. 1, wherein a pair of metal electrodes 102 and 104 are substituted for the liquid electrodes of FIG. 1. More specifically, the metal electrodes 102 and 104 are implanted preferably in the channel portion 40 and 48. In this modification, the fluid connections through the channel portions 40 and 48 of FIG. 1 are eliminated and the electrodes 102 and 104 are directly connected to the power source 86 and the detector 64 through a pair of conductors 106 and 108, respectively. For the purposes of claiming the invention, the opening 94 and 96, whether they be filled by liquid as in FIG. 1 or by metal as in FIG. 2, will be defined as electrode means consecutively positioned along the aperture 12. Although less desirable, the electrode means need not completely encircle the flow through the aperture 12.

A second embodiment of the invention is shown in FIGS. 3 and 4. In a similar manner to that of the first embodiment, the elongated hole 109 formed in the flow cell 10, which is upstream of the sensing zone, minimizes fluid acceleration. However, contrary to the two channel arrangement of the first embodiment, only the first annular chamber 36, with its channel portion 40 and cavity portion 38, is used. In this embodiment, the first annular chamber 36 is formed by mounting a sapphire wafer 110 against the body of the flow cell 10, so that a sensing orifice 112 is coaxially aligned with the elongated hole 109. For the purposes of defining the invention, the aperture 12 will be defined to include the elongated hole 109 and the orifice 112. Hence, as with the first embodiment, the channel portion 38 is defined as interrupting the aperture 12 with an annular opening.

The first annular chamber 36 could be fluidly and electrically connected to a remote chamber containing the electrode as shown in the first embodiment. However, the second embodiment shows an adaption of the invention for use in the present commercialized large particle processor of U.S. Pat. No. 4,140,966, which has been incorporated herein. In this arrangement, a director nozzle 114 provides a stream of particulate material into an upstream chamber 116 containing a liquid sheath 118, which hydrodynamically focuses the stream of particles. The electrode 80 is positioned in the chamber 116 and is in fluid communication directly with the aperture 12. Additionally, through a plurality of connecting tubes 120, the electrode 80 is fluidly connected to the annular chamber 36, which in turn opens into the aperture 12.

Contrary to the first embodiment of FIGS. 1 and 2, the connecting tubes 120 of the second embodiment shunts and therefore essentially "shorts out" the electrical and fluid path of the aperture 12 from its beginning to the channel portion 40. Although not shown in the preferred embodiment, the connecting tubes 120 can be filled with a non-conducting, fluid retarding material, such as a porous plastic or like porous dielectric material.

In contrast to the first embodiment of FIGS. 1 and 2, the aperture 12, and therefore the sensing zone, opens into the large fluid downstream chamber 122. The power electrode 84 is immersed in the electrolyte contained in the downstream chamber 122. Various known sweep flow systems can be used to prevent recirculating currents downstream of the sensing orifice 112, if desired.

As depicted in FIG. 3, the liquid sheath 118 is provided in a conventional manner through a plurality of apertures 123 formed in the director nozzle 114, which conveniently mounted in sealed relationship on the flow cell 10 by a pair of O-rings 124 and 126. A portion of the wall of the downstream chamber 122 is shown with phantom lines. Likewise a portion of the upstream chamber 116 is shown with phantom lines and contains the liquid sheath 118 which flows through the apertures 123. The power electrodes 80 and 84 are in fluid communication with the upstream and downstream chambers 116 and 122, respectively. Although they are shown positioned adjacent the flow cell 10, they can be remotely positioned with respect to the flow cell 10. The structure described in this paragraph is of a well known conventional design as shown in the heretoforementioned U.S. Pat. No. 4,140,966, and is only disclosed to the extent necessary to understand the present invention. However, it should be understood that there are numerous flow-through systems known to the art in which the flow cell 10 can be implemented, including the type described with the first embodiment wherein there is no liquid sheath for hydrodynamically focusing the sample suspension. Also, as with the first embodiment, a metal ring-like electrode can be used in place of the liquid in the channel portion 40, in a manner similar to that illustrated in FIG. 2. Although in the commercial embodiment, the aperture 12 is vertically aligned, it is horizontally aligned in FIG. 3 to illustrate that the flow cell is operable with any orientation desirable. The important phenomena of this flow cell 10 are gravity independent. FIG. 4 shows the end of the flow cell 10 with the wafer 110 removed so as to show the ends of the connector tubes 120.

Figure 5:
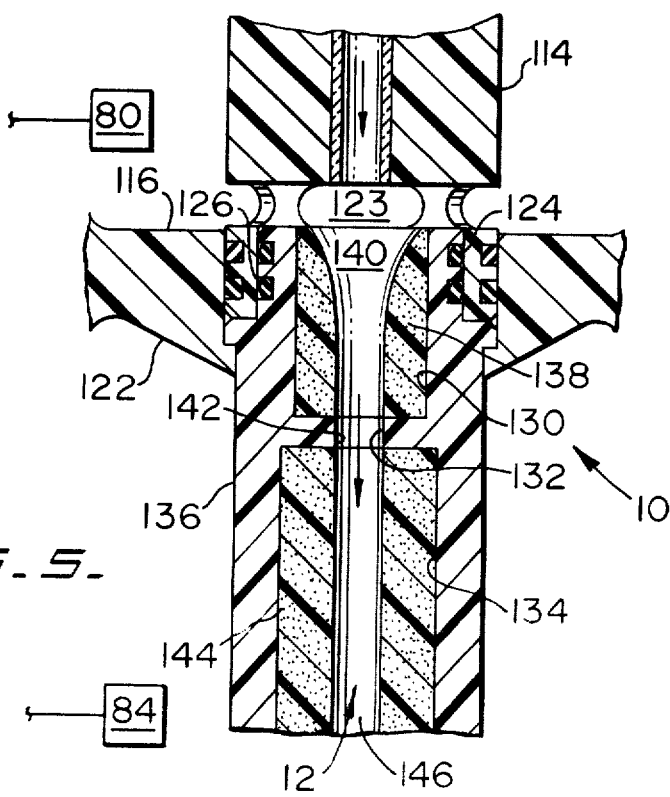
FIG. 5 is a cross-sectional view of a third embodiment of the flow cell.

FIG. 5 illustrates a third embodiment of the flow cell 10. Interiorly formed in the flow cell 10 are a first bore 130, a diameter restricting or blocking extension 132, and a second bore 134. With the extension 132 having for example, a 4000 micron inner diameter, the first and second bore would have a 15,000 micron diameter or greater, for example. The extension 132 would typically have a 4000 micron length along the axial length of the aperture 12. Preferably, but not necessarily, these three holes are annular in configuration and are defined by a main body 136 of the flow cell 10, which is preferably formed of a solid plastic. A first annular insert 138 is mounted in the first bore 130 and has formed therein an annular channel 140 which is gradually tapered from its entrance end so as to be substantially flush at its other end with the inner circumference of the extension 132. The annular insert 138 is formed from a porous plastic such as porous polyethylene, or like porous dielectric frit. This porous material is relatively transparent to electrical conduction, without electrode polarization effects, while at the same time resisting the passage of bulk fluid and/or particles. The extension 132 defines a sensing orifice 142 and has a substantially reduced diameter as compared to the bores 130 and 134. The second bore 134 has mounted therein a second annular insert 144, formed of the same material as the first annular insert 138. The insert 144 has a channel 146 therein, which is substantially flush with the sensing orifice 142. For the purposes of illustration, the flow cell 10 of the first embodiment is shown as being implemented in the same environment as the second embodiment; such environment being found in the heretofore mentioned U.S. Pat. No. 4,140,966. For the sake of simplicity, only portions of the director nozzle 114, the upstream chamber 116 and the downstream chamber 122 are shown. Although the use of the second bore 134 is preferred for eliminating recirculating flows, it can be eliminated as shown in the second embodiment. In such a case, the extension 132 would open directly into the downstream 122.

In operation, the liquid-filled annular inserts 138 and 144 have sufficiently low electrical resistance to transmit part of the electrical current between the electrodes 80 and 84. For the electrical current, the aperture 12 of the flow cell 10 becomes the first bore 130, the sensing orifice 142 and the second bore 134. On the other hand, the liquid flow is essentially confined to the interior of the annular inserts 138 and 144. Thus, for the liquid flow the aperture 12 becomes the channel 140, the sensing orifice 142 and the channel 146. Therefore, as with the other embodiments, a particle sensing zone in and around the sensing orifice 142 provides an electrical field with a relatively sharp edge, for good pulse response, while simultaneously providing a smooth fluid flow and inhibiting recirculation behind the sensing orifice 142.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzing apparatus for detecting the properties of particles, said particle analyzing apparatus including a container for holding a liquid suspension of the particles; a flow cell having an aperture formed therein; means for moving a sample of the liquid suspension through said aperture; means for providing an electrical field and current in said aperture to generate detectable electrical signals with the passage of the particles through said aperture; means for detecting the signals; the improvement comprising: said aperture of said flow cell having a tube-like configuration along its axial length, said aperture having an upstream end for receiving the sample and a downstream end whereat the sample exits; said means or providing said electric field and current comprising means for generating said field and current essentially only in a particle sensing portion of the axial length of said aperture, thereby defining said aperture to have a non-particle sensing portion extending from said upstream end of said aperture to said particle sensing portion; whereby said non-particle sensing portion of said aperture optimizes liquid accelerating, while said particle sensing portion of said aperture provides for a good signal response; said means for providing said electric field and current includes: an upstream electrode and a downstream electrode, means for providing electrical communication between said upstream electrode and the sample in said aperture at a position downstream of said upstream end of said aperture, means for providing electrical communication between said downstream electrode and the sample at a position downstream of said upstream electrode, and an electrical source for energizing said electrodes; said means for providing electrical communication for said upstream electrode includes a first channel formed in said flow cell for containing an electrolyte solution, and said means for providing electrical communication for said downstream electrode includes a second channel formed in said flow cell for containing an electrolyte solution, each said channel forming an opening into said aperture, said openings being positioned along the axis of said aperture in spaced-apart relationship with respect to each other, and each of said openings of said channels effectively surrounds the flow of the liquid suspension through said aperture.

2. The particle analyzing apparatus according to claim 1, wherein said non-particle sensing portion extends along the axial length of said aperture by a length greater than the length of which said particle sensing portion extends along the axial length of said aperture.

3. The particle analyzing apparatus according to claim 1, wherein said downstream electrode is in electrical communication with the sample in said aperture at a position upstream of said downstream end of said aperture, thereby defining a second non-particle sensing portion of said aperture.

4. The particle analyzing apparatus according to claim 1, wherein said means for providing electrical communication for said electrodes includes a pair of vessels, each for containing a quantity of an electrolyte solution; one of said electrodes being disposed in one of said vessels and the other said electrode being disposed in the other said vessel; one of said pair of vessels being in fluid communication with one of said pair of channels and the other said vessel being in fluid communication with the other said channel, whereby electrolyte products created around said electrodes in said vessels are substantially prevented from entering said aperture.

5. The particle analyzing apparatus according to claim 1 or 4, wherein said flow cell has formed therein a pair of ring-like cavities, one of said channels opening at its outer circumference into one of said cavities and the other said channel opening at its outer circumference into the other said cavity; each of said cavities having substantially greater cross-sectional dimensions than the cross-sectional width dimension of said channels; and further includes means for fluidly coupling said cavities to the respective said vessel.

6. The particle analyzing apparatus according to claim 1 or 4, wherein each said opening of said channels has a width dimension that is substantially smaller than the cross-sectional dimensions of said aperture.

7. The particle analyzing apparatus according to claim 1, wherein said means for providing electrical communication for said electrodes comprises said electrodes being embedded in the wall of said aperture in spaced-apart relationship with respect to each other.

8. The particle analyzing apparatus according to claim 7, wherein said electrodes completely surround the flow of the liquid suspension through said aperture.

9. The particle analyzing apparatus according to claim 1, wherein said downstream electrode is in fluid and electrical communication with said aperture through said downstream end of said aperture.

10. The particle analyzing apparatus according to claim 1, said upstream electrode being in direct fluid and electrical communication with said upstream end of said aperture and in fluid communication through a liquid path including said channel with said particle sensing portion of said aperture; said liquid path having a substantially lower electrical resistance than said non-particle sensing portion of said aperture so as to shunt the same.

11. The particle analyzing apparatus according to claim 1, wherein said opening of said channel has a width dimension, parallel to the longitudinal axis of said aperture, which is substantially smaller than the cross-sectional dimensions of said aperture, which are taken perpendicular to its longitudinal axis.

12. A particle analyzing apparatus for detecting the properties of particles, said particle analyzing apparatus including a container for holding a liquid suspension of the particles; a flow cell having an aperture formed therein; means for moving a sample of the liquid suspension through said aperture; means for providing an electrical field and current in said aperture to generate detectable electrical signals with the passage of the particles through said aperture; means for detecting the signals; the improvement comprising: said aperture of said flow cell having a tube-like configuration along its axial length, said aperture having an upstream end for receiving the sample and a downstream end whereat the sample exits; said means for providing said electric field and current comprising means for generating said field and current essentially only in a particle sensing portion of the axial length of said aperture, thereby defining said aperture to have a non-particle sensing portion extending from said upstream end of said aperture to said particle sensing portion; whereby said non-particle sensing portion of said aperture optimizes liquid accelerating, while said particle sensing portion of said aperture provides for a good signal response; said flow cell further including a first bore which extends inward from said upstream end of said aperture, a blocking extension positioned at the end of said first bore, said blocking extension defining therein a sensing orifice having smaller cross-sectional dimensions than the cross-sectional dimensions of said first bore so as to define a constricted electrical path, and a first insert member positioned in said first bore and formed of a porous dielectric material, said first insert member having formed therein a first channel which is aligned with and terminates into said sensing orifice so as to define a relatively continuous fluid path through said first channel and said sensing orifice.

13. The particle analyzing apparatus of claim 12, wherein said first channel has a tapered configuration with a decreasing diameter toward said blocking extension, said channel and said sensing orifice having substantially the same diameter at their juncture.

14. The particle analyzing apparatus of claim 12 or 13, wherein said flow cell includes further a second bore extending inward from said downstream end of said aperture and terminating with said blocking extension, said second bore having a substantially greater diameter than said sensing orifice; and a second insert member positioned in said second bore and formed of a porous dielectric material, said second insert member having formed therein a second channel which is aligned with and terminates into said sensing orifice so as to define a relatively continuous fluid path through said sensing orifice and said second insert member.

15. The particle analyzing apparatus of claim 14, wherein said sensing orifice and said second channel have substantially the same diameter at their juncture.

* * * * *